(12) United States Patent
Dixon et al.

(10) Patent No.: US 6,213,767 B1
(45) Date of Patent: Apr. 10, 2001

(54) INDIVIDUAL DOSE ADHESIVE DELIVERY AND ORTHODONTIC APPLIANCE SYSTEM

(75) Inventors: Daniel R. Dixon, Villa Park; Craig A. Andreiko, Alta Loma, both of CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/377,721

(22) Filed: Aug. 19, 1999

(51) Int. Cl.[7] ........................................... A61C 3/00
(52) U.S. Cl. ............................ 433/9; 206/369; 401/129
(58) Field of Search ............................ 433/8, 9, 4, 27; 206/572, 368, 369; 604/1; 401/129

(56) References Cited

U.S. PATENT DOCUMENTS

| | | | |
|---|---|---|---|
| 4,952,204 | * | 8/1990 | Korteweg .................................. 604/1 |
| 5,350,059 | * | 9/1994 | Chester et al. ............................ 433/9 |
| 5,354,199 | * | 10/1994 | Jacobs et al. ............................. 433/9 |
| 5,636,736 | * | 6/1997 | Jacobs et al. ......................... 206/369 |
| 5,660,273 | * | 8/1997 | Dicko, Jr. .............................. 206/229 |
| 5,756,174 | * | 5/1998 | Tuneberg ................................. 433/8 |
| 5,759,028 | * | 6/1998 | Bozman .................................... 433/9 |

* cited by examiner

Primary Examiner—Todd E. Manahan
(74) Attorney, Agent, or Firm—Wood, Herron & Evans, L.L.P.

(57) ABSTRACT

Individual orthodontic bracket doses of bracket adhesive are dispensed onto a flat resilient card and enclosed under a vapor proof cover sealed to the card. The cover is peeled off at chairside and individual orthodontic brackets pick up the individual doses of adhesive by a wiping of the adhesive doses by the orthodontist as the brackets are mounted on a patient's teeth. The card deforms to conform to the curvature of the edge of the appliance to cleanly transfer all of the adhesive of a dose from the card to the appliance base. On dose of adhesive is preferably provided for each tooth of a patient receiving a full set of orthodontic appliances. The individual doses are preferably divided into a bead of a basic dose with two small fractional supplemental dose beads to provide the orthodontist with the option of increasing the amount of adhesive on a given appliance. UV curable adhesive is dispensed onto the card as a single continuous bead while two part chemically curable adhesive is dispensed as a pattern of separate dots which do not combine until scooped up with the base of the appliance at the time of application. A sealed primer compartment is also provided on or with the card. Pads are provided on the card for mounting the appliances adjacent a corresponding adhesive dose. The appliances may be premounted by an appliance manufacturer and provided as a complete appliance system. Preferably, premounted appliances are provided on a separate card part that is connected to the adhesive bearing card at the time of use.

37 Claims, 8 Drawing Sheets

INDIVIDUAL DOSE ADHESIVE DELIVERY AND ORTHODONTIC APPLIANCE SYSTEM

This invention relates to the bonding of orthodontic appliances to teeth, and particularly, to the adhesive delivery systems for providing dental orthodontic adhesives for use in bonding appliances such as, for example, orthodontic brackets to the teeth of patients.

BACKGROUND OF THE INVENTION

With the development of orthodontic brackets such as those described, for example in U.S. Pat. No. 4,068,379, orthodontic brackets have replaced bands as the primary appliance for connecting orthodontic archwires to teeth. Unlike the banded appliances in which archwire supports mounted on bands that encircle teeth to hold the archwire supports in place on the teeth, brackets rely solely on an adhesive bond between the base or pad of the bracket and the surface of the crown of the tooth. Adequate bond strength between the teeth and the bracket bases has traditionally required the doctor or an assistant to dispense adhesive onto the bracket at chairside, using single or multiple part dental adhesives specifically developed for securing orthodontic appliances to teeth. Popular single part adhesives are cured by ultraviolet light, while multiple part adhesives cure chemically, following the mixing of the adhesive immediately preceding its use. The multiple part adhesives are often capable of producing bonds that are stronger than with the light cured adhesives.

The application of adhesives to brackets at chairside is a time consuming requirement. In preparing the adhesive at chairside, the quantity of adhesive dispensed must be carefully controlled by office personnel. Cleanup is required, which must be done by the doctor whose time is expensive. The handling of brackets during the application of adhesive can result in misorientation of the appliances and a mixup of the appliances, which are usually designed to fit specific teeth.

One attempt to minimize the chairside handling of adhesives in the application of orthodontic appliances to teeth has been the introduction of orthodontic brackets with light cured adhesive pre-applied to the bracket bases. While these brackets with pre-applied adhesive are attractive to orthodontists for their promise of convenience and ease of installation on the teeth of the patient, such brackets have been associated with an increased failure rate of the bond between the bracket bases and the teeth.

One cause of failures of the bonds between the bracket and a tooth is due to the use of an adhesive beyond its actual shelf life. The shelf life of adhesive that has been pre-applied to brackets is optimistically claimed to be twenty-four months. In practice, environmental factors, such as heat, humidity, etc., during transit and storage of the brackets having the pre-applied adhesives, shortens the shelf life of the adhesive. Furthermore, orthodontic brackets with adhesives pre-applied seldom reach the offices of orthodontists immediately following manufacture, so that some portion of the shelf life of the adhesive is already spent by the time the brackets are received by the orthodontist. In addition, careful records and careful inventory control by the doctor is required to insure that all adhesively pre-coated brackets are used in a FIFO basis and before the adhesive becomes too old.

Orthodontic brackets are often stocked by orthodontists in sufficient quantities so that the doctor has available appliances of various types and sizes to use on any common occasion in the treatment of patients. Maintaining appliance inventories necessarily requires that certain appliances will be in inventory longer than others. Ordinarily, orthodontic brackets are made of metal or other materials that have a shelf life that exceeds the technological life of the appliance, that is, the appliance can usually be stored until it is used or becomes obsolete, which can be many years from the stocking of the appliance by the doctor. Orthodontic brackets have a cost of several dollars to the doctor, for example, four U.S. dollars per bracket at the time of this patent application. The cost of the adhesive used to secure orthodontic brackets to teeth is substantially less expensive than the ordinary bracket, from a few cents to about a seventy-five cent per bracket price premium charged by an adhesively pre-coated bracket manufacturer. As a result, the application of a few cents worth of adhesive imposes a limited shelf life on a relatively expensive orthodontic appliance.

There are additional disadvantages to the adhesively pre-coated orthodontic appliances currently available on to orthodontists. The packaging of such appliances, for example, is quite expensive to produce and bulky. One hundred cases, for example, might occupy several cubic feet of space in a dentist office, equal, for example, to that of a small appliance or piece of furniture. Individual brackets are packaged in sealed packages which must be individually opened at chairside. Appliance delivery systems cannot readily accommodate these brackets or bracket packages, and separate systems for dispensing adhesive primer must be used. Only one part, light curable adhesives, can be pre-applied to brackets. Use of multiple part adhesives, which can be up to thirty percent stronger, are not practical with such brackets. Furthermore, when the amount of pre-applied adhesive appears to be incorrect in a particular situation, there is no easy way to adjust the quantity.

Accordingly, there is a great need on the part of orthodontic practitioners for a system for easily and conveniently applying orthodontic appliances to teeth with adhesive that does not have all of the disadvantages of the pre-adhesively coated orthodontic brackets of the prior art.

SUMMARY OF THE INVENTION

A primary objective of the present invention is provide to an orthodontic practitioner the advantages that adhesively pre-coated brackets have over the chairside application of adhesive from bulk sources to orthodontic appliances. A further objective of the present invention is to overcome the disadvantages of the adhesively pre-coated brackets of the prior art.

According to principles of the present invention, single appliance doses of orthodontic adhesive are provided separate from the orthodontic appliances that the adhesive is designed to apply. According to particular principles of the invention, individual doses of adhesive are provided in a form for direct transfer to the bases of orthodontic appliances at chairside. According to further principles of the invention, individual adhesive doses are packaged for easy use, and are presented in combination with, or in an arrangement by which they can be easily associated with, specific orthodontic appliances for each of the teeth of a patient.

In accordance with certain principles of the present invention, there is provided an orthodontic adhesive delivery system and method in which a substrate is provided on which one or more single dose amounts of orthodontic adhesive are supported in a way as to be effectively transferred to the base of the appliance by contact of the appliance with the substrate, preferably by a swiping motion of the appliance along the substrate to efficiently scrape the adhesive from the substrate surface. The substrate is preferably provided with a resilient core and a non-stick, non-absorbent, vapor-proof, flexible surface. At least one, and preferably one for each appliance of an appliance set, single-appliance-dose quantity of adhesive is pre-dispensed onto the substrate surface. The preferred adhesive is a non-volatile liquid orthodontic dental adhesive. Each dose is pre-dispensed onto an adhesive transfer area on the adhesive supporting surface of the substrate. The adhesive is contained in a cavity over the substrate by a vapor-proof cover that is sealed to the substrate surface so as to form a raised enclosure covering the adhesive transfer area or areas of the adhesive supporting surface. Preferably, a plurality of separate cavities is formed between the cover and the substrate surface, one for each of the adhesive transfer areas and each containing one single dose amount of the adhesive. Preferably, the cover is configured so as to remain out-of-contact with the adhesive on the adhesive transfer areas of the substrate surface. The cover may be configured to open the cavities and expose the doses individually or several or all simultaneously.

In accordance with preferred embodiments of the invention, an orthodontic appliance holder is provided, one for each adhesive transfer area, and each holder is configured to hold an orthodontic appliance in a ready position relative to a dose of adhesive for easy pickup by an orthodontist. One holder is preferably provided for the support of each appliance needed to treat a particular patient at a particular sitting. In certain embodiments of the invention, an orthodontic appliance is also provided and preferably a set of appliances is provided, one associated with each adhesive transfer area containing a single appliance dose of adhesive, providing the orthodontist with a complete orthodontic appliance system of the components needed to treat a case. All of the doses may be provided of the same adhesive quantity or the doses may be varied in accordance with the requirements for the different appliances of the set. The appliances may, in certain embodiments, be provided pre-attached, one to each holder. Preferably, the appliances are provided physically separate from the substrate bearing the adhesive, and may be provided on holders that are separate or detachable from the substrate bearing the adhesive. The appliances, where provided, are also preferably individually wrapped in their own sanitary containers and are positioned and oriented in their packages for easy pickup by the practitioner.

The system of the preferred embodiment of the invention is further provided with a sealant in a quantity suitable for preparing the teeth on which appliances are to be applied by the adhesive on the substrate. Single or multiple part sealers may be used, and each part is provided in a separate container either affixed to or separate from the substrate, along with such brushes or other applicators as may be convenient.

In certain preferred embodiments of the invention, the doses of adhesive are deposited onto the surface of the substrate in a strip that is narrower than the width of an appliance base in contact with the substrate surface. The strip is of a length containing a volume of adhesive that is nominally an amount for application of a single appliance to a tooth, for example, a minimum quantity sufficient to effectively bond an appliance to a tooth. In addition, separate measured supplemental amounts, preferably one or two in number, each equal to about one tenth of the nominal volume, are deposited on each transfer area of the substrate surface in line with, but separated from, the main nominal adhesive dose. This allows the clinician the option of increasing the nominal main dose by ten or twenty percent on an appliance-by-appliance basis.

In certain preferred embodiments of the invention, a single dose adhesive such as typical light curable adhesives may be used and deposited on the transfer areas of the substrate surface in a contiguous strip. In alternative embodiments, multiple part adhesives may be deposited on the transfer areas of the substrate surface in separate fragmentary amounts such as in dot arrays, for example, by printing spots of each component in interleaved arrays on the substrate surface, in a pattern that lies in a line that is of a width less than the width of an appliance in contact with the substrate surface.

In the preferred embodiment of the invention, the substrate is formed in multiple layers, including an inner core of a thickness of a resilient foam material covered by a film of polyethylene or comparable non-stick flexible material. The cover is preferably also formed of multiple layers, preferably including a polymer layer and a foil layer.

In use, the doctor first opens and applies the sealant to the tooth of a patient. Then, the doctor removes the cover from a substrate on which the dose or doses of adhesive needed for treatment are deposited, exposing the adhesive. The appliance is then picked up, preferably from a holder attached to the substrate carrying the adhesive which holds a specific appliance for installation on a specific tooth of a patient. The appliance so picked up, for example, with tweezers or special tool, is scraped along the pattern of adhesive in one of the transfer areas of the substrate surface, causing the adhesive deposited on the transfer area of the surface to be cleanly removed from the substrate surface and transferred onto the base of the appliance. With a single part adhesive, the appliance is placed on the tooth and, if appropriate, the adhesive is light cured. With the multiple part adhesive, the scraping and removal of the adhesive from the substrate surface causes the separate amounts of the different parts of the adhesive to be thoroughly mixed together so that, upon application onto the surface of the tooth, the adhesive is sufficiently mixed to properly chemically cure.

The delivery system and method of the present invention provides the advantage that orthodontic adhesive, even though not pre-dispensed, can be easily picked up directly by the appliance. Further, the adhesive can be picked up by the appliance in a quantity that is either predetermined at, or that can be adjusted about, a nominal adhesive volume. As a result, the clinician is provided with control over the quantity of adhesive required in varying clinical situations, minimizing cleanup due to excess or minimizing the need for rebonding due to failure from inadequate adhesive.

With the delivery system of the present invention, the adhesive is not attached to the appliance or associated with its package, and thus the shelf life of the adhesive does not impose a shelf life on the substantially more expensive appliance. The adhesive system of the present invention presents a low cost package of single dose adhesives in a form that can be disposed of separate from the appliances when an adhesive expiration date is reached. Further, the adhesive package, according to preferred embodiments the present invention, is inexpensive and occupies very little space in shipping or in the office of the practitioner.

The preferred embodiments of the invention further provide the advantages of single dose adhesive units, one for each appliance required to treat a single patient, and in a package by which all individual dose units can be opened at once, with minimal handling by the doctor or staff. In certain embodiments of the invention, adhesive primer is provided in a disposable, no-mix, non-light cure form. Further, certain embodiments of the invention provide adhesive light cure as well as multiple part chemical cure compositions. In additional embodiments, individual appliances are packaged in association with each of the single adhesive doses, which may vary in size from appliance-to-appliance.

These and other objectives and advantages of the present invention will be more readily apparent from the following detailed description of the drawings of the preferred embodiment of the invention, in which:

DETAILED DESCRIPTION OF THE DRAWINGS

Figure 1:
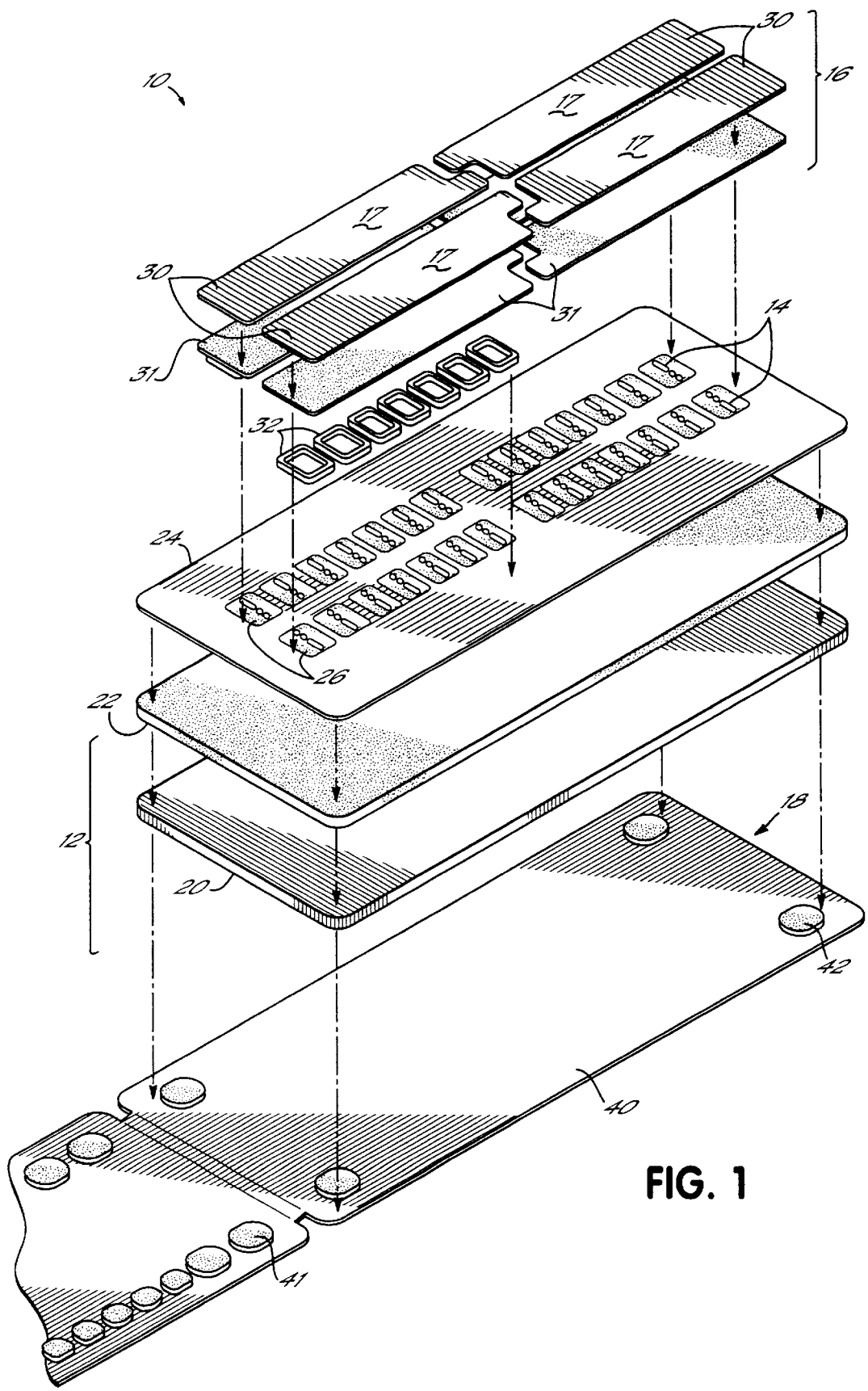
FIG. 1 is a disassembled isometric view of an orthodontic adhesive delivery system according to one preferred embodiment of the invention.
Figure 1A:
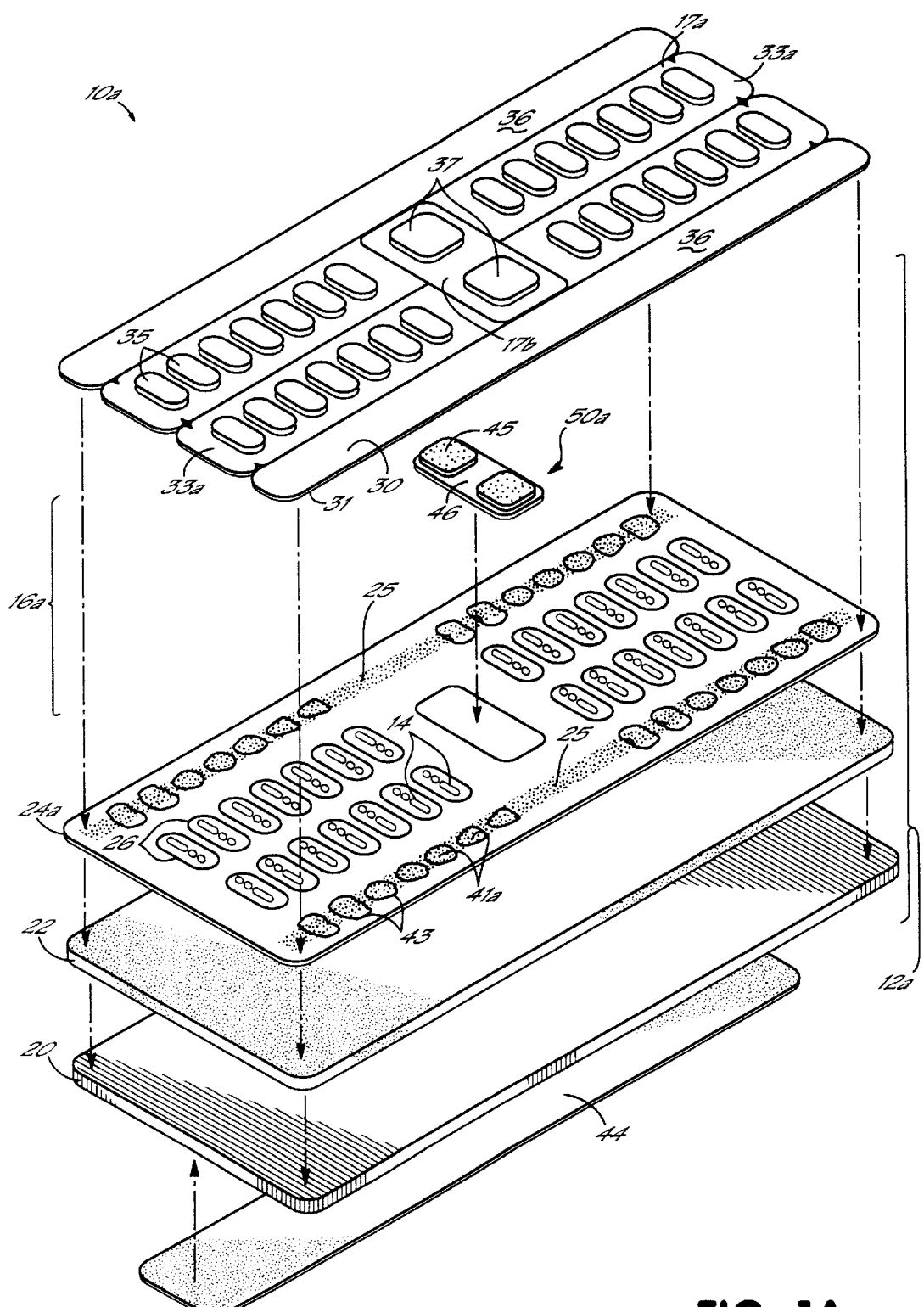
FIG. 1A is a disassembled isometric view, similar to FIG. 1, of an orthodontic adhesive delivery system according to another preferred embodiment of the invention.

The adhesive delivery system of the present invention is illustrated and described in two embodiments, embodiment 10 illustrated in part in FIG. 1, and embodiment 10a, illustrated in part in FIG. 1A. Referring to the embodiment of FIG. 1, the system 10 has four primary components, which include a substrate assembly 12, single dose amounts of bracket bonding adhesive 14, an adhesive cavity cover and seal 16, and outer packaging and mounting structure 18.

Figures 6A, 6B:
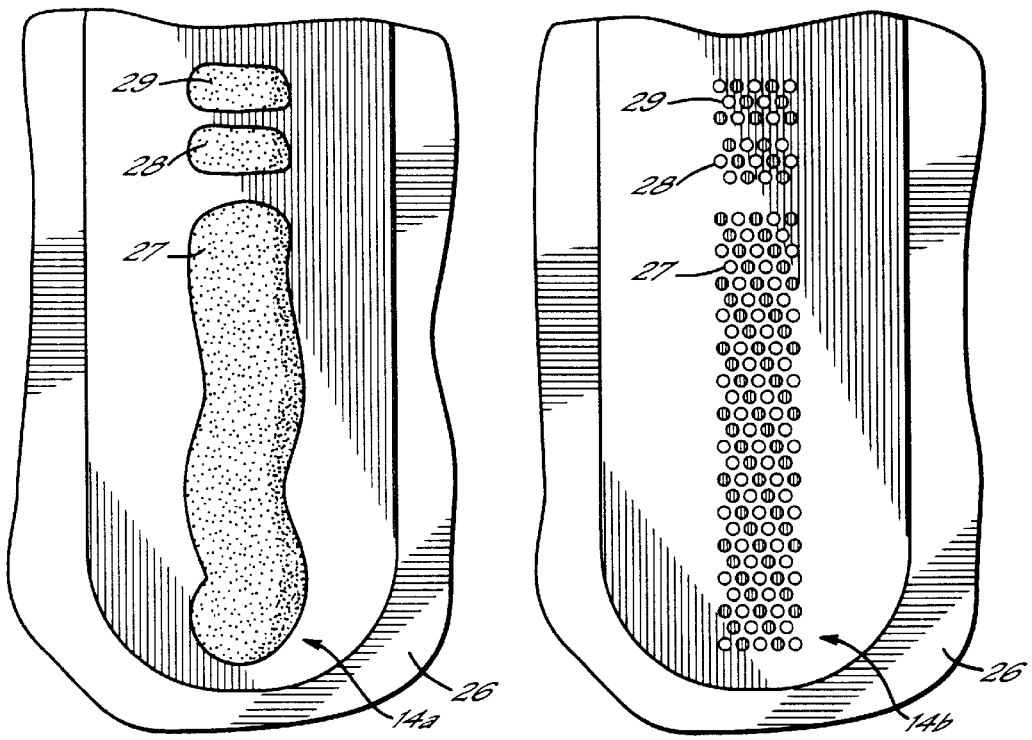
FIG. 6A plan view illustrating a dose of adhesive of the single part type on a transfer area of the surface of the substrate of the system of FIG. 1 or 2.
FIG. 6B plan view, similar to FIG. 6A, illustrating a dose of adhesive of the two part type on a transfer area of the surface of the substrate of the system of FIG. 1 or 2.
Figure 7A:
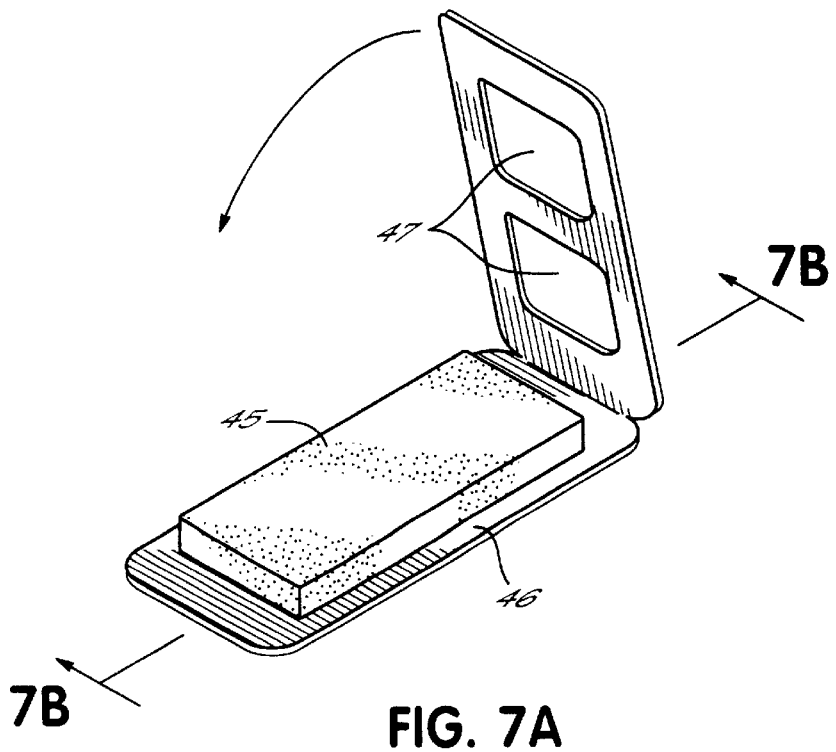
FIG. 7A is a perspective view of a sealant package portion of the system embodiment of FIG. 2.
Figure 7B:
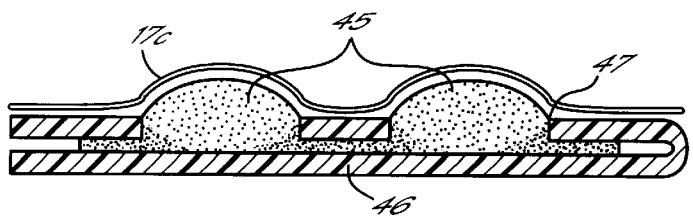
FIG. 7B is a cross-sectional view of the sealant package portion of FIG. 7A.
Figure 6C:
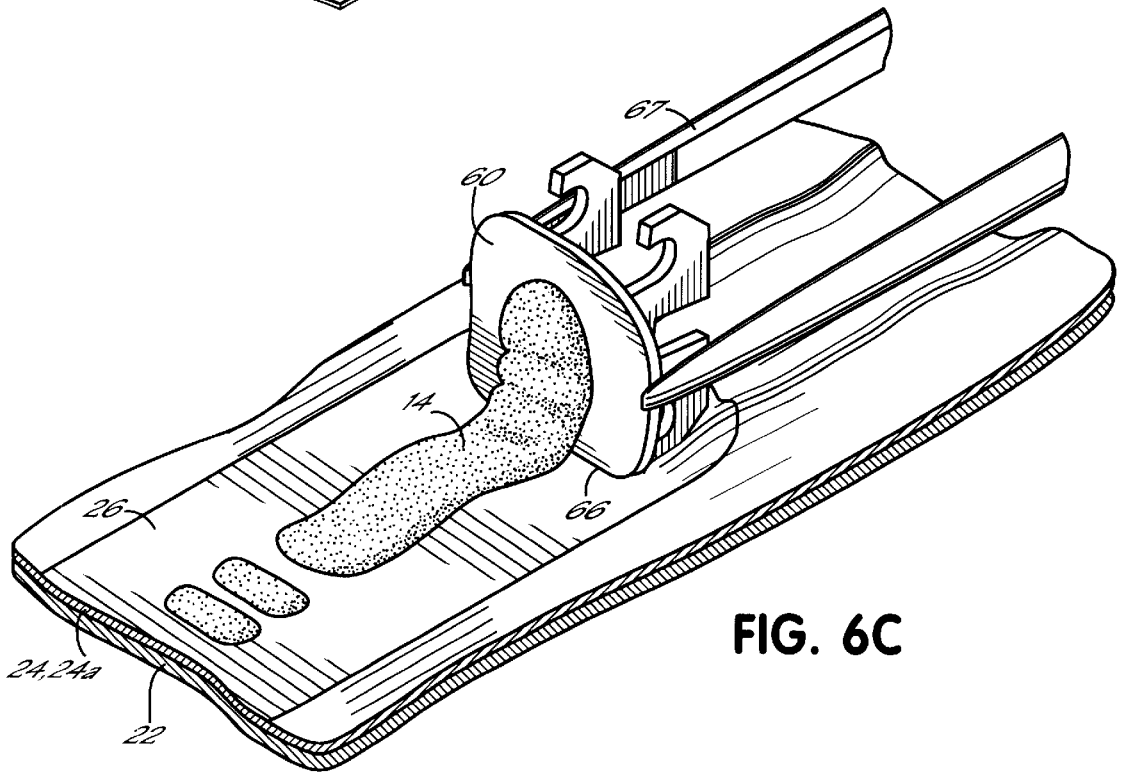
FIG. 6C illustrates the scooping of the adhesive from the substrate with the base of an appliance and the transfer of adhesive from the substrate to the base.

The substrate assembly 12, which is sometimes referred to herein as simply the substrate, is formed three layers, including a backing layer 20 of sheet material, an inner layer 22 of compliant or compressible material and an adhesive supporting surface layer 24 of a non-stick, flexible, relatively impervious material 26. The base layer 20 may be a paper or cardboard layer, a layer of PVC or other plastic, or another material that will give the substrate 12 a degree of stiffness and flatness. The backing layer 20 is, for most such materials, preferably approximately 20–25 mills (0.02–0.025 inches) in thickness. The inner compliant or compressible layer 22 is formed preferably of a polymeric foam material, preferably approximately 20–25 mils thick. The surface layer 24 is preferably formed of a material such as polyethylene film approximately 2–3 mils in thickness. The surface layer 24 is flexible and slippery to allow the edge of an orthodontic appliance to easily slide over the surface of the substrate. The inner core layer 22 is compressible, being designed to be deformed by the convex edge of a bracket base or pad being slid over the film layer 24 on the surface of the substrate 12 so that the substrate conforms to the shape of the perimeter of the base so that the pad can cleanly scoop up the adhesive as it is slid over the surface of the substrate 12, as illustrated in FIG. 6C. As shown in FIG. 6C, an orthodontic appliance in the form of an orthodontic bracket 60 is being held with tweezers 67 and its convex edge 66 is used to cleanly scoop up the adhesive dose 14 on a transfer area 26 of a substrate 12,12a by pressing the convex appliance edge 66 against the surface layer 24,24a of the substrate 12,12a as the core 22 is compressed.

The surface of the substrate 12 has a plurality of adhesive supporting and transfer areas 26 at which the slippery film layer 24 is exposed. The film layer 24 may be colored a dark color or preferably is clear in the transfer areas 26 to expose the inner foam layer 22, which is preferably black. This coloration allows the light colored opaque or translucent adhesive 14 to be clearly visible against the dark background of the surface of the substrate 12 at the areas 26. In manufacture, the layers 20, 22 and 24 are permanently laminated together and the periphery of the substrate 12 is then die cut to the final shape of the substrate 12, preferably to a rectangular shape approximately 2–3 inches in width to 5–7 inches in length.

Once the substrate 12 is formed, a single dose of orthodontic appliance adhesive is deposited onto each of the transfer areas 26 on the surface of the substrate 12. Such an adhesive is preferably a Bisphenol A-Glycidyl Methacrylate type adhesive having a low vapor pressure and of a consistency resembling that of modeling clay, and which is catalyzed by a free radical mechanism. Both light cure and chemical cure adhesives are suitable for the individual doses of the adhesive 14. Such adhesives are preferably dispensed in one long line 27, followed by two short lines 28 and 29, each equal to about ten percent of the length of the long line, as better illustrated in FIGS. 6A and 6B, and all at about 10–15 mils in width and height. This allows the orthodontist to pick up either only the long line 27, which provides a predetermined nominal amount of adhesive which is not too much for any appliance, or to pick up ten or twenty percent more than the nominal amount by picking up one or both of the short lines 28 and 29 of adhesive, respectively, as the orthodontist may deem most clinically advantageous. Different numbers or sizes of additional lines 28,29 or supplemental amounts of adhesive may be provided in combination with a various sizes of a long line 27 or main amount of adhesive, in order to provide a proper predetermined nominal amount or range of options for the orthodontist.

The light cure adhesive, which is typically provided a single part adhesive, is dispensed onto the transfer areas 26 of the substrate 12 as a homogeneous bead that needs no mixing prior to use. Such a homogeneous bead is illustrated as bead 14$a$ in FIG. 6A. The chemical cure adhesive is dispensed as an array of separate component dots, illustrated as A dots and B dots in FIG. 6B. With the chemical cure adhesive, the shear and rolling of the dots as they are scooped by the edge of an orthodontic appliance 60, as illustrated in FIG. 6C, mixes the two different dot components. Furthermore, as the chemical cure adhesive components are squeezed between the appliance base and the surface of a tooth as the appliance is applied to the tooth, additional mixing of dots A and B occurs. In addition, chemical cure adhesive will pick up residual catalyst from the primer-sealant that is already on the tooth, further enhancing the curing of the adhesive. Diffusion gradients exist all through the mixing and application processes, contributing to the mixing of the A and B components and the distribution of catalyst to affect a cure of the adhesive without more manual mixing than described above.

Around each of the individual adhesive dose transfer areas 26, a seal is formed between the cover 16 and the substrate 12 that is effective to stop the loss of any volatile components of the adhesive and to provide complete darkness to insure that no premature light curing or light induce degradation of the adhesive takes place. In the embodiment of FIG. 1, the cover 16 includes a foil layer 30, a polymer layer 31 and a foam layer 32. The foil layer may be, for example, a 2 mil thick layer of aluminum foil, which will fold sharply at the beginning of each successive foam seal 32 to keep the seal out of the way of the operator while appliance adhesive is being accessed. The polymer layer may be, for example, a 0.5 mil thick layer of polyethylene film effective to prevent contamination of the adhesive by the foil and to provide a non-stick surface to present to the adhesive in the event that it does touch the seal. The foam layer 32 may be in the form of a set of rectangular windows, each formed of a 20–25 mil thick polyethylene foam and bonded to the polymer layer 31 so as to surround the perimeter of each of the transfer areas 26 when the cover 12 is situated over the substrate 12. The lower surface of the foam layer 32 is coated with pressure sensitive adhesive having properties that provide a bond between the foam layer 32 of the cover 16 and the substrate 12 that is weaker than the bond between the foam layer 32 and the polymer layer 31 of the cover 16. The individual window like components of the foam layer 32 on the cover 16 each individually surround the periphery of one of the transfer areas 26. The foam layer 32 is of a thickness that prevents the cover from contacting the adhesive doses 14 on the surface 24 of the substrate 12.

The cover 16 may be formed in one or more parts 17, which are shown as four parts 17 in number in the drawings, with each part 17 covering seven of the individual adhesive doses of adhesive 14 associated with each tooth of one of the four upper or lower, right or left half arches of a patient. These parts 17 are preferably formed by die cutting the cover 16 after the three layers 30–32 are laminated together. The four parts 17 of the cover 16 are placed on the substrate 12 with release tabs 33 arranged to allow random opening of any one of the parts 17.

The system 10 is also provided with an outer packaging component 40 which carries printed information and graphics and supports adhesive holders 41 for the mounting of appliances to be installed on the patient with the adhesive doses 14 as well as adhesive mounting feet 42 for enabling the fixing of the substrate 12 to tray or other structure to hold it in place during use. The packaging layer 40 may be fabricated from metallized MYLAR of, for example, about 2 mils in thickness. The non-foil side of the packaging layer 40 faces outwardly and contains printing and graphics while the foil side has mounted thereto a plurality of adhesive mounting pads 41, one corresponding to each of the adhesive transfer areas 26, for supporting the appliance that is to be applied to a specific one of the teeth of a patient with the adhesive dose 14 supported on the surface 24 of the substrate 12 at the associated transfer area 26.

The pads 41 are arranged on the packaging layer 40 so as to contact the surface 24 of the substrate 12 when the packaging layer 40 wrapped around the substrate 12. The side of the pad 31 away from the packaging layer 40 are coated with pressure sensitive adhesive that forms a stronger bond than adhesive joining the pads 41 to the packaging layer 40, so that the pads 41 transfer to and remain with the substrate 12 when the packaging layer 40 is removed. Similarly, the feet 42 are bonded to the packaging layer 40 so as to transfer to the bottom of the substrate 12 to form bonding feet to hold the substrate 12 to a work surface such as a tray or table.

Figure 2:
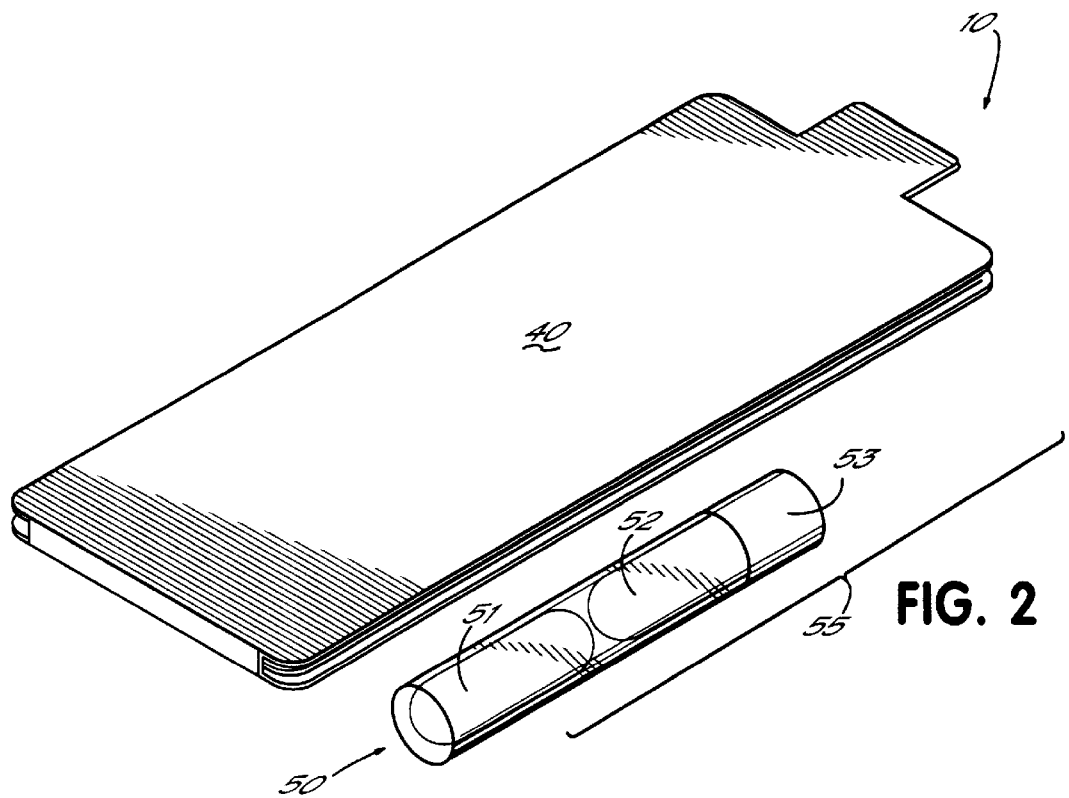
FIG. 2 is an assembled isometric view of an orthodontic adhesive delivery system according to one preferred embodiment of the invention incorporating the embodiment of FIG. 1 in a form packaged for shipping or storage.

The pads 41 are 10–15 mils thick and formed of white polyethylene double sided self-adhesive foam to stand out against a darker background of the fundamental substrate 12. Each pad is preferably shaped to look like the en-face view of the crown of a specific tooth of a patient to visually synchronize not only with the tooth to which an appliance is to be bonded but to correspond in shape with that of the base of a corresponding appliance such as those described in commonly assigned U.S. patent application Ser. No. 08/933, 269 filed Jul. 22, 1996 by the inventor hereof, hereby expressly incorporated by reference herein. The feet are about 5 mils in thickness, also formed of self-adhesive double-sided polyethylene. The packaging layer 40 is shown in FIG. 2 in a closed condition around a substrate 12, and is shown in FIG. 3 in an opened condition exposing the cover 16 sealed onto the substrate 12 and the appliance holder pads 41 transferred and affixed to the outer edges of surface layer 24 of the substrate 12 so that one pad 41 is immediately adjacent to and associated with each one of the transfer areas 26 that carry a dose of adhesive 14 for the installation of an appliance that can be supported on the corresponding pad 41.

In the embodiment of FIGS. 1–5, there is provided an ampule 50 containing a sealer-primer for the pre-coating of the teeth to which the adhesive doses 14 are to be applied for securing appliances to the teeth. The ampule 50 contains two glass vials 51,52 respectively containing the same resin and catalysts as would be used in the A and B type two-part chemical curing adhesive, but having a lower viscosity and molecular weight, with no glass filler material, whereby it is more flowable than such an adhesive. The primer contains a fast drying solvent to lower the viscosity of the sealer-primer and to, by evaporation, limit the thickness of the primer left on the tooth. The ampule 50 also has, at one end thereof, a wick 53. Crushing of the ampule 50 breaks the vials 51,52 within the ampule 50 and allows the two A and B parts of the sealer-primer to mix and wet the wick 53. With the wick 53, the mixed sealer-primer can be transferred to the surface of a tooth, where it wets the etched surface of the tooth on which it is applied, and achieves a chemical bond with the bracket adhesive 14 when the adhesive coated appliance is placed on the tooth. The system 10 along with the ampule 50 constitute a complete appliance application kit 55.

Figure 3:
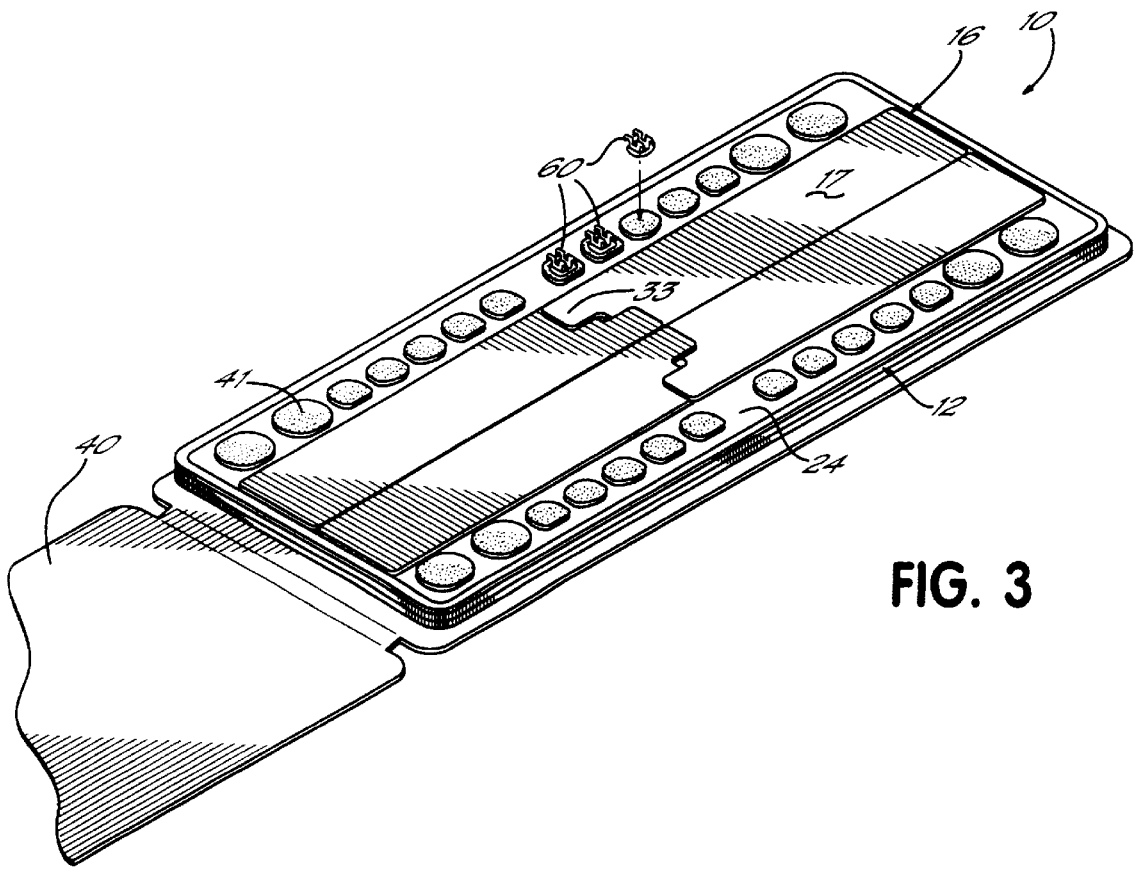
FIG. 3 is an isometric view, similar to FIG. 2, of an orthodontic adhesive delivery system of the embodiment of FIG. 1 prepared for use.

When the system 10 is uncovered for use by an orthodontist or assistant, as illustrated in FIG. 3, orthodontic appliances may be assembled onto each of the pads 41. The unique appliance designed for a specific tooth of a patient, are associated with specific doses of adhesive 14 on one of the transfer areas 26, and placed on the pad 41 adjacent the transfer area 26 carrying the associated adhesive dose 14. Illustrated are orthodontic brackets 60 for an upper right central and upper right lateral secured to their respective associated pads 41 with a bracket for an upper right central positioned to be secured to its associated pad 41. Such appliances 60 may be applied to the pads 41 at the orthodontists office, or may be preapplied by the appliance manufacturing or supplying company and delivered to the orthodontist as a complete assembled appliance installation package of appliances 60 and either a system 10 or a kit 55 that includes a system 10 along with a sealer-primer ampule 50.

Figure 4:
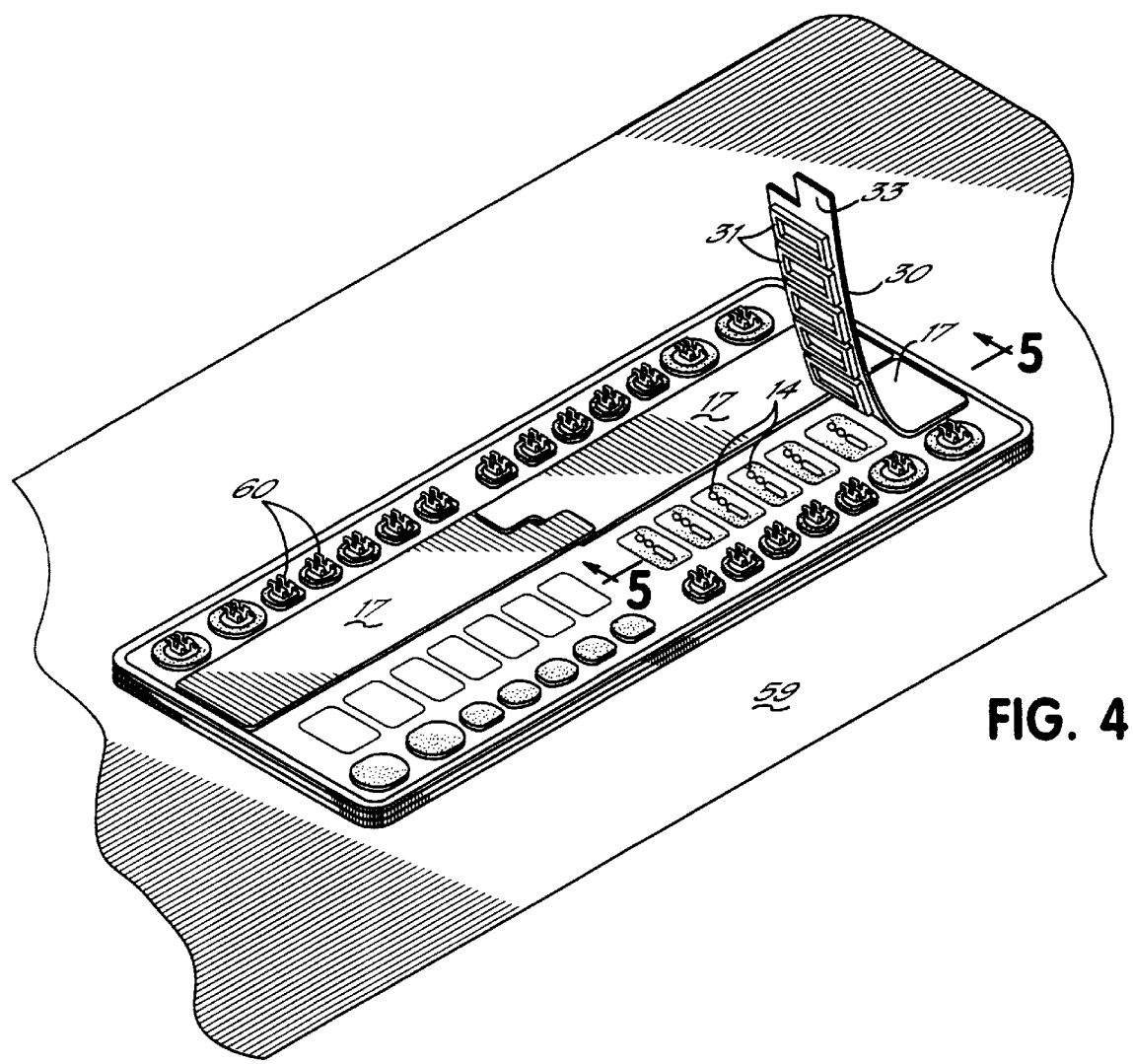
FIG. 4 is an isometric view, similar to FIG. 3, of an orthodontic adhesive delivery system of the embodiment of FIG. 1 in use.
Figure 5:
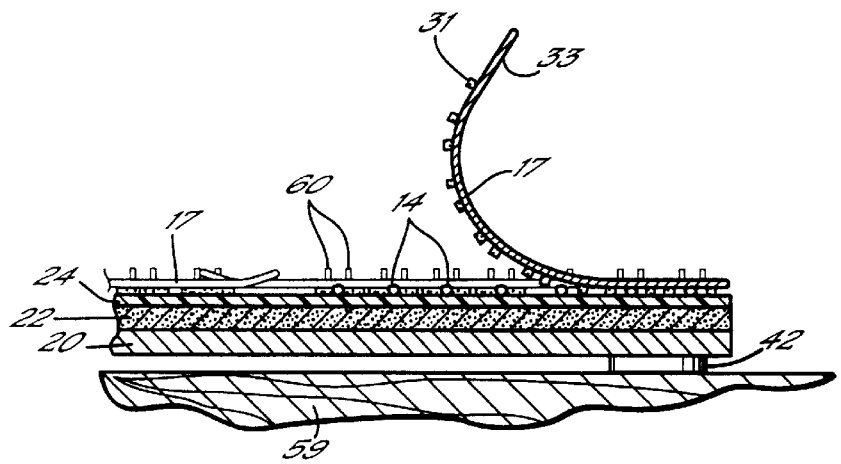
FIG. 5 is a cross-sectional view taken along the line 5—5 of FIG. 4.

Use of the system 10 is illustrated in FIGS. 4 and 5, which show a system 10 mounted on a table or tray 59 as might be adjacent a chair in an orthodontists office, with one of the parts 17 of the cover 16 being opened. In the drawings, the adhesive 14 and appliances 60 for the lower right arch of the patient have already been applied, with the part 17 of the cover 12 being removed to expose the adhesive 14 for the lower left arch of the patient.

An alternative embodiment to the system 10 described above is adhesive delivery system 10a illustrated in FIGS. 1A–5A. Referring to the embodiment of FIG. 1A, the system 10a has three primary components, which include a substrate assembly 12a, the single dose amounts of bracket bonding adhesive 14 and an adhesive cavity cover and seal 16a. Outer packaging is not necessary or may include simply a sleeve or envelope (not shown) to contain the system 10a and bear printed information and graphics.

The substrate assembly 12a, is formed three layers 20, 22 and 24a as in the case of the substrate 12 described above. The surface layer 24a of the substrate 12 has the plurality of adhesive supporting and transfer areas 26 on each of which one of the single doses adhesive 14 is applied of either the single part light curable type or the two part chemical curable type as illustrated in FIGS. 6A and 6B. Appliance holder positions 41a are formed on directly on the surface layer 24a by preprinted outlines or profiles 43 of each of a patient's teeth covered by strips 25 of pressure sensitive adhesive dispensed onto the layer 24a over the printed tooth outlines 43. The outlines 43 of the holder positions 41a are printed on the surface layer 24a oriented 90° to the orientations of the pads 41 in the embodiment described above so that the appliances 60, when positioned and oriented on the outlines 43 as they would be when properly located on the corresponding tooth of the patient, are positioned for easy pickup by the orthodontist with the use of tweezers.

In the embodiment of FIG. 1A, a cover 16a, provided to form a seal with the substrate 12 around each of the transfer areas 26, differs from the cover 16 described above. The cover 16a includes the foil layer 30 and polymer layer 31, but, instead of foam layer 32, the cover 16a is deformed into single dose adhesive covering pockets 35 that are 20–25 mils deep to avoid contact with the adhesive doses 14 while permitting the side of cover 16a having polymer layer 31 thereon to directly contact and seal to the surface layer 24a of the substrate 12a. The foil layer 30 be a 2 mil thick layer of aluminum foil and the polymer layer may be a 0.5 mil thick layer of polyethylene film.

The cover 16a is preferably die cut with score lines into four parts 17a, with each part 17a covering seven of the individual adhesive doses of adhesive 14 associated with each tooth of one of the four upper or lower, right or left half arches of a patient. The four parts 17 of the cover 16 are placed on the substrate 12 with release tabs 33 arranged to allow random opening of any one of the parts 17. Edge strips 36 are similarly die cut from the cover 16a to provide separately removable covers for the adhesive strips 25.

The substrate 12a of system 10a are provided with an adhesive base 42a to permit the bottom of the substrate 12a to be removably attached to and held in position on an orthodontist's tray. The adhesive base 42a is covered with a removable strip of silicone treated paper 44.

Figure 2A:
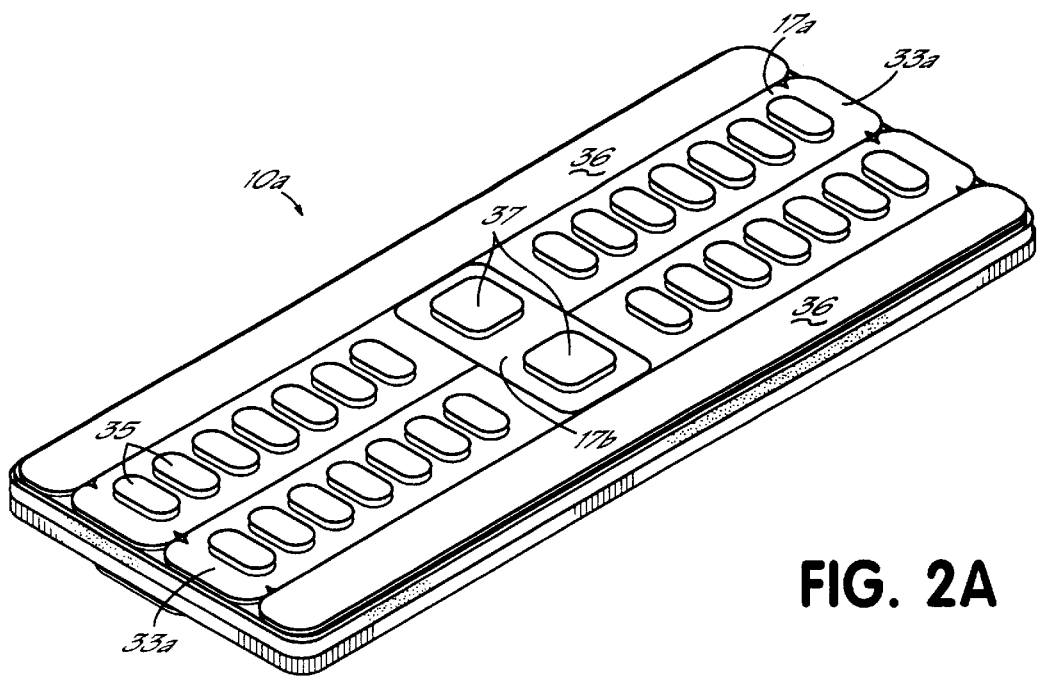
FIG. 2A is an assembled isometric view of an orthodontic adhesive delivery system according to one preferred embodiment of the invention incorporating the embodiment of FIG. 1A.

In the embodiment of FIGS. 1A–5A, there is provided an pouch 50a containing sealer-primer for the pre-coating of the teeth to which the adhesive doses 14 are to be applied for securing appliances to the teeth. The pouch 50 contains core 45 of polyurethane foam or other absorbent carrier material, which may be in one or more pieces to contain a one part sealer primer or which may be formed of at least two pieces, one containing the same resin and one the catalyst that would be used in the A and B type two-part chemical curing adhesive. The pouch 50a is formed by a plastic folded envelop 46 having a window 47 in one side thereof that is smaller than the dimension of the foam core 45 so that the envelop 46 can be folded over and trap the foam core 45 so as to allow the foam core 45 to project outwardly from the window 47. A cover for the pouch 50a is formed by die cutting an area 17b in the center of the cover 16a with one or more raised pockets 37 therein in the center. The envelop 46 with the core 45 therein is assembled is then bonded to the center of the surface layer 24a of the substrate 12a and the sealed pouch 50a is completed when the cover 16a is sealed to the surface layer 24a of the substrate 12a, where the periphery of the area 17b is sealed with releasable adhesive to the surface layer 24a of the substrate 12a or to the envelop 46 around the core 45. Alternatively, in lieu of using the envelop 46, the core 45 may be bonded directly to the surface layer 24a of the substrate 12a. A fully assembled and sealed system 10a is illustrated in FIG. 2A.

Figure 4A:
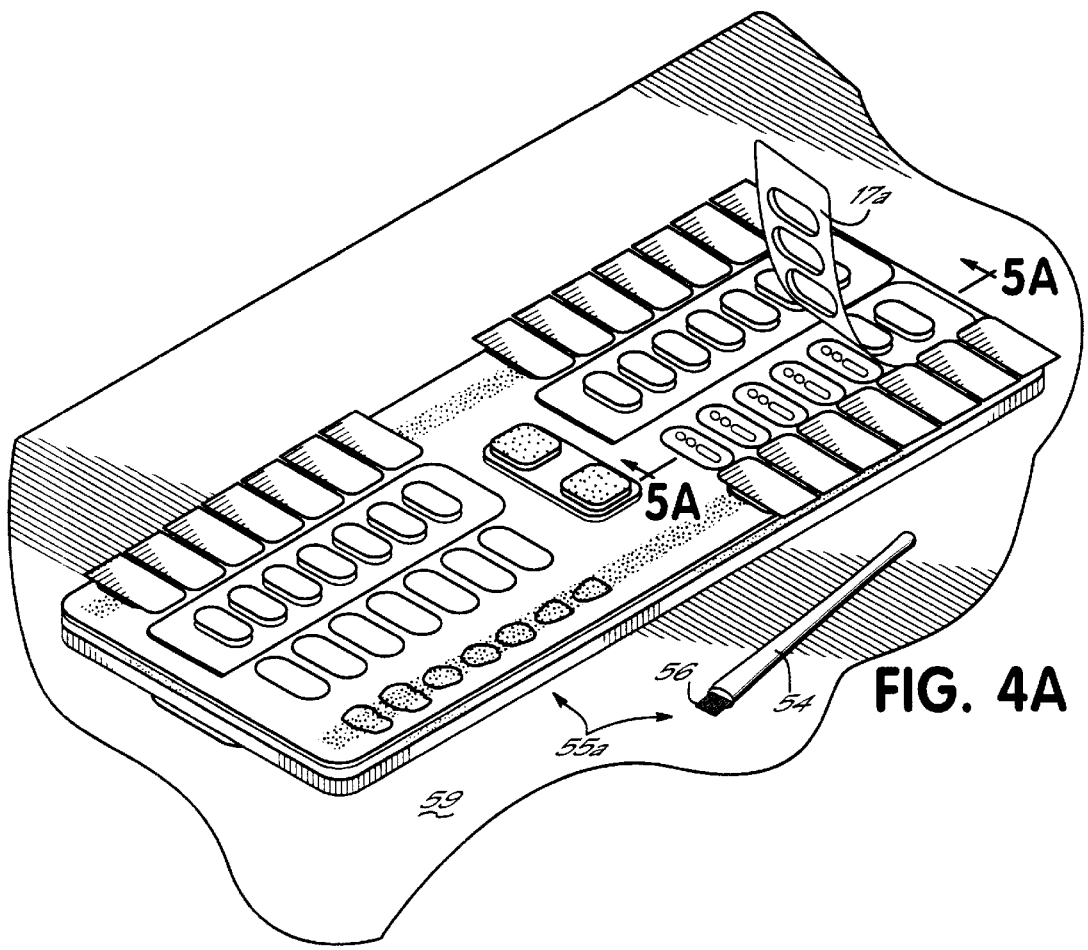
FIG. 4A is an isometric view, similar to FIG. 3A, of an orthodontic adhesive delivery system of the embodiment of FIG. 2 in use.

A brush or applicator 54 is separately provided to form a kit 55a as illustrated in FIG. 4A. By dipping the tip 56 of the brush or applicator 55a against the exposed foam core 44, the sealer-primer can be transferred to the teeth.

Figure 3A:
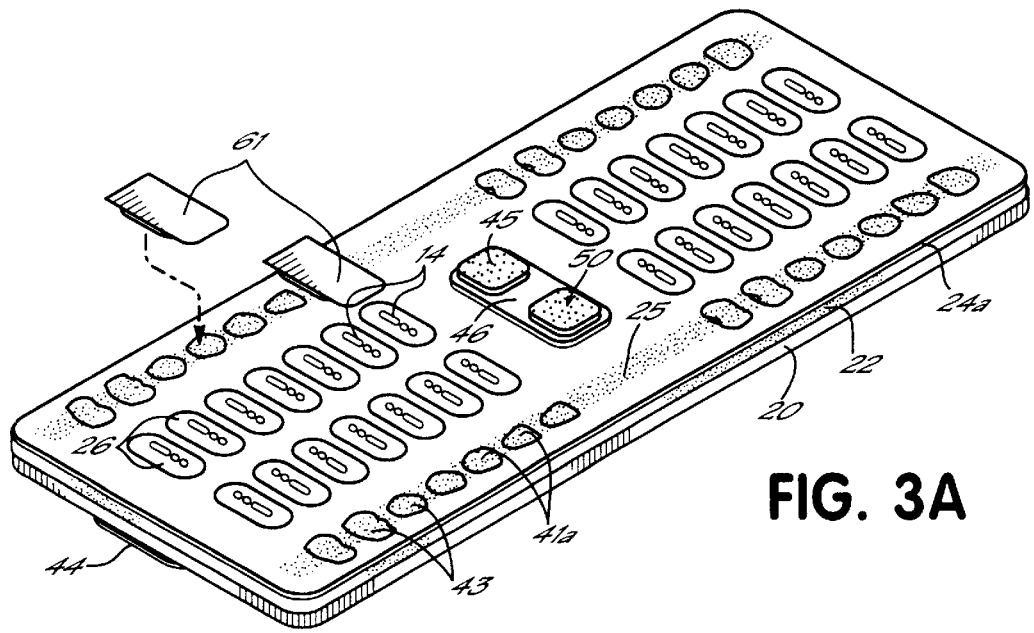
FIG. 3A is an isometric view, similar to FIG. 2A, of an orthodontic adhesive delivery system of the embodiment of FIG. 2 prepared for use, and with individual prepackaged orthodontic appliances provided in association with the respective adhesive doses.

In lieu of mounting orthodontic appliances 60 directly to the substrate 12,12a, the appliances 60 may be contained in individual packages 61. These packages 61 may be similar to blister packs of the type used to individually package pills, as illustrated in FIG. 3A. Such packages 61 can be adhered to the appliance support positions 41a on the surface layer 24a of the substrate 12a or on the supports 41 of the embodiment of the system 10 of FIGS. 1–5 described above.

Figure 5A:
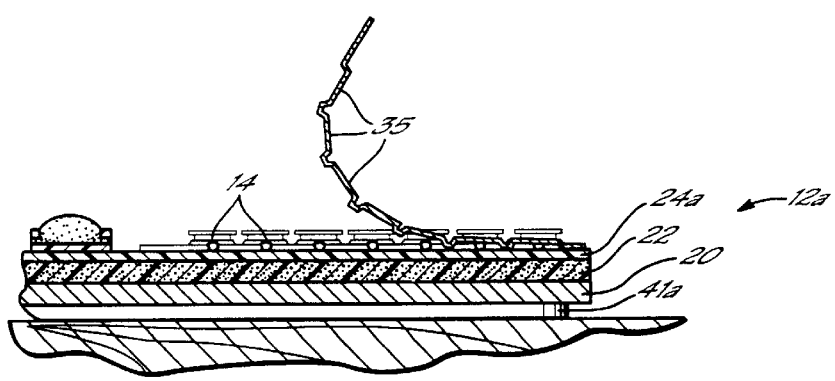
FIG. 5A is a cross-sectional view taken along the line 5A—5A of FIG. 4A.

Use of the system 10a is illustrated in FIGS. 4a and 5a, which show a system 10a mounted on a table or tray 59 adjacent a chair in an orthodontists office, with one of the parts 17a of the cover 16a being opened. Use of the system 10a is similar to that described above for the embodiment of system 10.

Figure 8:
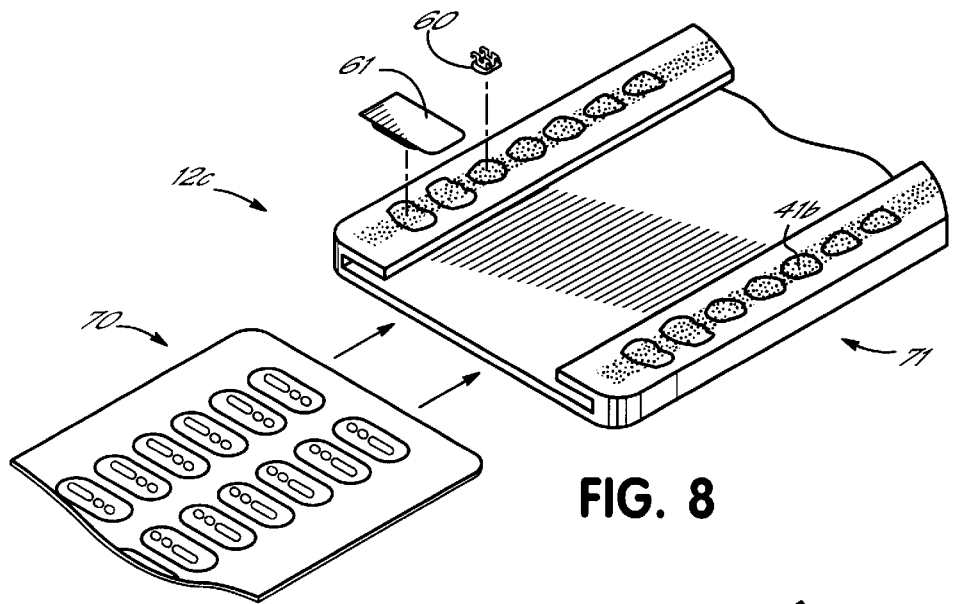
FIG. 8 is an isometric view of a substrate portion of the embodiments of the system of FIG. 1 or 2 with orthodontic appliances mounted as a set, separate from the adhesive bearing substrate, and in one manner in which the appliances and adhesive doses are associated.

While in the embodiments described above pads 41 or mounting positions 41a are provided for supporting appliances next to associated adhesive doses, the substrate 12,12a can alternatively be provided as two part cards 12b, with a substrate card 70 carrying the adhesive doses 14 being supplied separate from an appliance mounting card 71 with appliances 60 or prepackaged appliances 61 mounted, and preferably premounted, thereon on mounting areas 41b, as illustrated in FIG. 8. In this way, mounted sets of appliances can be delivered by an appliance manufacture to an orthodontist who can stock an assortment of these relatively long lived and relatively expensive appliance set assemblies, while the shorter shelf lived and relatively inexpensive adhesive delivery systems can be acquired more often and stored for less time. When a case is ready for treatment, the adhesive carrying card 70 can be inserted into a slot in the appliance mounting card 71.

Those skilled in the art will appreciate that the application of the present invention herein is varied, that the invention is described in preferred embodiments, and that additions and modifications can be made without departing from the principles of the invention.

Therefore, the following is claimed:

1. An orthodontic adhesive delivery system comprising:
   a substrate having an adhesive supporting surface having at least one adhesive transfer area;
   at least one single-appliance dose quantity of orthodontic dental adhesive on the at least one adhesive transfer area; and
   a cover sealed to the substrate and separating the adhesive from and maintaining the adhesive out of contact with an appliance while so sealed so as to form at least one enclosure covering at least one adhesive transfer area of the adhesive supporting surface of the substrate and containing the at least one single dose of adhesive.

2. An orthodontic appliance system including the delivery system of claim 1 and further comprising:
   an orthodontic appliance holder associated with a single dose quantity of orthodontic dental adhesive, the holder being configured to hold an orthodontic appliance thereto in a ready position in relation to the transfer area on which the quantity of adhesive is supported; and
   an orthodontic appliance attachable to the holder and maintained out of contact with the adhesive.

3. The orthodontic appliance system of claim 2 further comprising: a single appliance package having the appliance sealed therein and attachable to the holder.

4. The orthodontic adhesive delivery system of claim 1 wherein:
   the at least one adhesive transfer area includes a plurality of seaprate adhesive transfer areas;
   the at least one single-appliance dose quantity of orthodontic dental adhesive includes a plurality of single-appliance dose quantities of orthodontic dental adhesive, each supported on a separate one of the plurality of adhesive transfer areas on the adhesive supporting surface of the substrate.

5. The delivery system of claim 4 further comprising:
   a plurality of orthodontic appliance holders, each associated with a different one of the single dose quantities of orthodontic dental adhesive, each holder being configured to hold an orthodontic appliance thereto in a ready position in relation to the transfer area on which the quantity of adhesive is supported.

6. An orthodontic appliance system comprising the delivery system of claim 5 and further comprising:
   a plurality of orthodontic appliances, one attached to each holder and each associated with a different one of the separate adhesive transfer areas.

7. The orthodontic appliance system of claim 6 further comprising:
   a plurality of single appliance packages each having one of the appliances sealed therein and each affixed to a different one of the holders.

8. An orthodontic appliance system including the delivery system of claim 1 and further comprising:
   at least one holding area on the substrate configured for to be loaded with an orthodontic appliance container;
   a sealed orthodontic appliance container having an orthodontic appliance contained therein, the container configured to be loadable onto the holding area on the substrate to hold an orthodontic appliance to the substrate separate from and out of contact with the single-appliance dose quantity of orthodontic dental adhesive.

9. The orthodontic adhesive delivery system of claim 1 wherein:
   the cover is an open-once cover sealed to the substrate so as to form an enclosure covering the at least one adhesive transfer area of the adhesive supporting surface of the substrate and containing the at least one single dose of adhesive and that is effective to protect the adhesive prior to the opening of the cover.

10. An orthodontic adhesive delivery kit comprising the delivery system of claim 1 and further comprising:
    an encapsulated liquid primer.

11. The orthodontic adhesive kit of claim 10 wherein:
    the encapsulated liquid primer includes a sealed openable pouch secured to the surface of the substrate and having liquid primer component.

12. The orthodontic adhesive kit of claim 11 wherein:
    the sealed pouch has an absorbent carrier material therein soaked with the liquid primer component.

13. The orthodontic adhesive delivery system of claim 1 wherein:
    the adhesive supporting surface of the substrate is deformable.

14. The orthodontic adhesive delivery system of claim 1 wherein:
    the single dose quantity of orthodontic adhesive is dispensed onto the transfer area in an elongated configuration including at least a nominal minimum quantity sufficient to effectively bond an appliance to a tooth.

15. The orthodontic adhesive delivery system of claim 14 wherein:
    the single dose quantity of orthodontic adhesive is a light curable adhesive.

16. The orthodontic adhesive delivery system of claim 1 wherein:
    the cover is an open-once, adhesive-protecting cover sealed to the substrate so as to form an enclosure covering the at least one adhesive transfer area of the adhesive supporting surface of the substrate and containing the at least one single dose of adhesive.

17. The orthodontic adhesive delivery system of claim 16 wherein:
    the adhesive-protecting cover is sealed to the substrate so as to form an enclosure that protects the adhesive from contact by a curing medium for at least the stated shelf life of the adhesive.

18. The orthodontic adhesive delivery system of claim 16 wherein:
   the adhesive is curable by exposure to ultraviolet light; and
   the adhesive-protecting cover is sealed to the substrate so as to shield the adhesive on the substrate from contact by ultraviolet light.

19. The orthodontic adhesive delivery system of claim 1 wherein:
   the substrate has a plurality of adhesive transfer areas on the adhesive supporting surface thereof;
   the at least one single-appliance dose quantity of orthodontic dental adhesive includes a plurality of single dose quantities, one for each of a plurality of appliances and one on each of a plurality of the adhesive transfer areas on the adhesive supporting surface of the substrate; and
   the cover is an open-once, adhesive protecting cover sealed to the substrate configured to form a plurality of sealed enclosures, one covering each of the adhesive transfer areas of the adhesive supporting surface of the substrate and containing one of the single doses of adhesive.

20. An orthodontic liquid primer delivery system comprising:
   a substrate having a sealed openable pouch surrounded by a pouch wall having liquid primer component therein, the pouch having an absorbent carrier material therein soaked with the liquid primer component and expanded into contact with the surrounding pouch wall.

21. A orthodontic adhesive delivery system comprising:
   a substrate having an adhesive supporting surface;
   a quantity of orthodontic dental adhesive on the adhesive supporting surface of the substrate; and
   a cover sealed to the substrate enclosing the adhesive;
   the quantity of orthodontic dental adhesive being chemically curable adhesive having multiple parts, each part being deposited in a different one of a plurality of physically distinct regions on the substrate.

22. A method of supplying an orthodontic adhesive comprising:
   providing a substrate having an adhesive supporting surface;
   dispensing at least one single-appliance dose quantity of orthodontic dental adhesive onto an adhesive transfer area on the adhesive supporting surface of the substrate; and
   enclosing the single-appliance dose quantity of the orthodontic adhesive on the adhesive supporting surface with a cover by sealing the cover to the substrate and forming a an enclosure covering the adhesive transfer area of the adhesive supporting surface and containing the single dose of adhesive so as to separate the adhesive from, and maintain the adhesive out of contact with, an appliance.

23. A method of providing an orthodontic appliance including supplying an adhesive according to the method of claim 22 and further comprising:
   providing an orthodontic appliance holder configured to hold an orthodontic appliance thereto in a ready position in relation to the transfer area on which the quantity of adhesive is supported; and
   providing an orthodontic appliance attached to the holder.

24. The method of providing an orthodontic appliance adhesive of claim 22 wherein:
   the dispensing of a single-appliance dose quantity of orthodontic dental adhesive includes dispensing a plurality of single-appliance dose quantities of orthodontic dental adhesive, each onto a separate adhesive transfer area on the adhesive supporting surface of the substrate.

25. A method of providing an orthodontic appliance including supplying an adhesive according to the method of claim 22 and further comprising:
   providing a plurality of orthodontic appliance holders, each configured to hold an orthodontic appliance thereto in a ready position in relation to the transfer area on which the quantity of adhesive is supported; and
   attaching a plurality of orthodontic appliances, one to each holder.

26. The method of providing an orthodontic appliance adhesive of claim 22 wherein:
   the dispensing of single dose quantity of orthodontic adhesive includes dispensing adhesive onto the transfer area in an elongated pattern including at least a nominal minimum quantity sufficient to effectively bond an appliance to a tooth.

27. A method of providing an orthodontic appliance comprising:
   supplying an adhesive by:
      providing a substrate having a non-stick, non-absorbent, vapor-proof, flexible, deformable adhesive supporting surface,
      dispensing at least one single-appliance dose quantity of orthodontic dental adhesive onto an adhesive transfer area on the adhesive supporting surface of the substrate, and
      enclosing the single-appliance dose quantity of the orthodontic adhesive between the adhesive supporting surface and the substrate and a vapor-proof cover by sealing the cover to the substrate and forming a raised enclosure covering the adhesive transfer area of the adhesive supporting surface and containing the single dose of adhesive;
   providing a plurality of orthodontic appliance holders, each configured to hold an orthodontic appliance thereto in a ready position in relation to the transfer area on which the quantity of adhesive is supported;
   attaching a plurality of orthodontic appliances, one to each holder; and
   the dispensing of the single dose quantity of orthodontic adhesive includes dispensing adhesive onto a transfer area in a pattern that includes a nominal dose quantity of adhesive and one or more separate supplemental fractional dose quantities spaced from the nominal dose.

28. An orthodontic adhesive delivery system comprising:
   a substrate having an adhesive supporting surface having at least one adhesive transfer area,
   at least one single-appliance dose quantity of orthodontic dental adhesive on the at least one adhesive transfer area; and
   a cover sealed to the substrate so as to form at least one enclosure covering the at least one adhesive transfer area of the adhesive supporting surface of the substrate and containing the at least one single dose of adhesive;
   the substrate being formed in at least two parts, including a first part having the transfer areas thereon and a second part having the holders thereon, each part being physically connectable to the other so as to constrain holders in ready positions relative to each of the transfer areas on which a quantity of adhesive is supported.

29. An orthodontic adhesive delivery system for presenting one or more individual single-appliance doses quantities of adhesive for pickup and transfer to an orthodontic appliance, the system comprising:
a substrate having an adhesive supporting surface having at least one adhesive transfer area thereon at which said surface is conformable to an edge of an object during transfer of adhesive to an appliance by the scooping of the adhesive from the surface with the object;
at least one single-appliance dose quantity of orthodontic dental adhesive on the at least one adhesive transfer area; and
a cover sealed to the substrate so as to form at least one enclosure covering at least one adhesive transfer area of the adhesive supporting surface of the substrate and containing the at least one single dose of adhesive.

30. The orthodontic adhesive delivery system of claim 29 wherein said object is the orthodontic appliance to which the single-appliance dose quantity of the adhesive is to be transferred, and wherein:
the surface is conformable to an edge of an orthodontic appliance base during transfer of adhesive to an appliance by the scooping of the adhesive from the surface with the appliance.

31. An orthodontic adhesive delivery system comprising:
a substrate having an adhesive supporting surface having at least one adhesive transfer area;
at least one single-appliance dose quantity of orthodontic dental adhesive on the at least one adhesive transfer area; and
a cover sealed to the substrate so as to form at least one enclosure covering the at least one adhesive transfer area of the adhesive supporting surface of the substrate and containing the at least one single dose of adhesive;
the encapsulated liquid primer including an ampule having a wick applicator end and containing one or more fracturable vials containing a component of the primer.

32. A method of adhesively bonding an orthodontic appliance to the tooth of a patient comprising:
providing a substrate having an adhesive supporting surface having at least one adhesive transfer area having a single-appliance dose quantity of orthodontic dental adhesive enclosed beneath a cover thereon;
removing the cover to expose the adhesive on the adhesive supporting surface of the substrate;
transferring the adhesive from the surface and onto an orthodontic appliance; and
bonding an appliance with the adhesive thereon to the surface of a tooth of the patient.

33. The method of claim 32 wherein:
the transferring of the adhesive includes scraping the adhesive from the surface by sliding an edge of an object against the surface and deforming the surface in conformity therewith to scoop the single-appliance dose quantity of adhesive from the substrate with the object.

34. The method of claim 32 wherein:
the transferring of the adhesive includes scraping the adhesive from the surface by sliding an edge of the appliance against the surface of the substrate and deforming the surface in conformity therewith to scoop the single-appliance dose quantity of adhesive from the substrate and onto the appliance.

35. An orthodontic adhesive delivery system comprising:
a substrate having an adhesive supporting surface having at least one adhesive transfer area;
at least one single-appliance dose quantity of orthodontic dental adhesive on the at least one adhesive transfer area; and
a cover sealed to the substrate so as to form at least one enclosure covering the at least one adhesive transfer area of the adhesive supporting surface of the substrate and containing the at least one single dose of adhesive;
the single dose quantity of orthodontic adhesive being dispensed onto one or more of the transfer areas in a pattern including a nominal dose quantity of adhesive and one or more separate supplemental fractional doses spaced from the nominal dose.

36. An orthodontic adhesive delivery system comprising:
a substrate having an adhesive supporting surface having at least one adhesive transfer area;
at least one single-appliance dose quantity of orthodontic dental adhesive on the at least one adhesive transfer area; and
a cover sealed to the substrate so as to form at least one enclosure covering the at least one adhesive transfer area of the adhesive supporting surface of the substrate and containing the at least one single dose of adhesive;
the single dose quantity of orthodontic adhesive being dispensed onto the transfer area in an elongated configuration including at least a nominal minimum quantity sufficient to effectively bond an appliance to a tooth; and
the single dose quantity of orthodontic adhesive being a multiple part chemically curable adhesive having the parts each dispensed in a physically distinct region in the configuration on the substrate.

37. A method of providing an orthodontic appliance comprising:
supplying an adhesive by:
providing a substrate having a non-stick, non-absorbent, vapor-proof, flexible, deformable adhesive supporting surface,
dispensing at least one single-appliance dose quantity of orthodontic dental adhesive onto an adhesive transfer area on the adhesive supporting surface of the substrate, and
enclosing the single-appliance dose quantity of the orthodontic adhesive between the adhesive supporting surface and the substrate and a vapor-proof cover by sealing the cover to the substrate and forming a raised enclosure covering the adhesive transfer area of the adhesive supporting surface and containing the single dose of adhesive;
providing a plurality of orthodontic appliance holders, each configured to hold an orthodontic appliance thereto in a ready position in relation to the transfer area on which the quantity of adhesive is supported;
attaching a plurality of orthodontic appliances, one to each holder; and
forming a supplemental substrate part having the holders thereon, the supplemental part being physically connectable to the substrate so as to constrain appliances on the holders in ready positions relative to each of the transfer areas on which a quantity of adhesive is supported.

* * * * *

UNITED STATES PATENT AND TRADEMARK OFFICE
CERTIFICATE OF CORRECTION

PATENT NO.    : 6,213,767 B1
DATED         : April 10, 2001
INVENTOR(S)   : Dixon et al.

It is certified that error appears in the above-identified patent and that said Letters Patent is hereby corrected as shown below:

Title page,
Title reads "INDIVIDUAL DOSE ADHESIVE DELIVERY AND ORTHODONTIC APPLIANCE SYSTEM" and should read -- INDIVIDUAL DOSE ADHESIVE DELIVERY SYSTEM, ORTHODONTIC APPLIANCE SYSTEM AND METHOD OF PROVIDING AND USING SAME --.
ABSTRACT reads "On dose of adhesive" and should read -- One dose of adhesive --.

Column 2,
Line 20, reads "available on to orthodontists" and should read -- available to orthodontists --.
Line 44, reads "invention is provide to an" and should read -- invention is to provide an --.

Column 3,
Line 66, reads "one tenth" and should read -- one-tenth --.

Column 4,
Line 62, reads "embodiments the present invention" and should read -- embodiments of the present invention --.

Column 5,
Line 49, reads "FIG. 6A plan view" and should read -- FIG. 6A is a plan view --.
Line 52, reads "FIG. 6B plan view" and should read -- FIG. 6B is a plan view --.
Lines 55 and 64, read "of FIG. 1 or 2" and should read -- of FIGS. 1 or 2 --.

Column 6,
Line 12, reads "is formed three layers" and should read -- is formed of three layers --.
Line 20, reads "20-25 mills" and should read -- 20-25 mils --.

UNITED STATES PATENT AND TRADEMARK OFFICE
CERTIFICATE OF CORRECTION

PATENT NO.    : 6,213,767 B1
DATED         : April 10, 2001
INVENTOR(S)   : Dixon et al.

It is certified that error appears in the above-identified patent and that said Letters Patent is hereby corrected as shown below:

Column 7,
Line 9, reads "with a various" and should read -- with various --.
Line 12, reads "provided a single part" and should read -- provided as a single part --.
Line 37, reads "light induce degradation" and should read -- light induced degradation --.
Line 52, reads "when the cover 12 is" and should read -- when the cover 16 is --.
Line 58, reads "window like" and should read -- window-like --.

Column 8,
Line 26, reads "are coated" and should read -- is coated --.
Line 38, reads "en-face" and should read -- enface --.
Line 36, reads "double sided" and should read -- double-sided --.

Column 9,
Line 13, reads "The unique appliance" and should read -- The unique appliances --.
Lines 23 and 31, read "orthodontists office" and should read -- orthodontist's office --.
Line 47, reads "is formed three layers" and should read -- is formed of three layers --.

Column 9,
Line 54, reads "formed on directly on" and should read -- formed directly on the --.

Column 10,
Line 7, reads "layer 30 be a" and should read -- layer 30 may be a --.
Line 19, reads "system 10a are provided" and should read -- system 10 a is provided --.
Line 25, reads "provided an pouch" and should read -- provided a pouch --.
Line 31, reads "sealer primer" and should read -- sealer-primer --.
Lines 35, 37, 41, 48 and 49, read "envelop" and should read -- envelope --.
Line 42, reads "is assembled is then" and should read -- is assembled then --.
Line 65, reads "FIGS. 4a and 5a" and should read -- FIGS. 4A and 5A --.
Line 67, reads "orthodontists office" and should read -- orthodontist's office --.

UNITED STATES PATENT AND TRADEMARK OFFICE
CERTIFICATE OF CORRECTION

PATENT NO. : 6,213,767 B1
DATED : April 10, 2001
INVENTOR(S) : Dixon et al.

It is certified that error appears in the above-identified patent and that said Letters Patent is hereby corrected as shown below:

Column 11,
Line 13, reads "appliance manufacture to an" and should read -- appliance manufacturer to an --.

Column 13,
Line 55, reads "forming a an enclosure" and should read -- forming an enclosure --.

Signed and Sealed this

Second Day of April, 2002

*Attest:*

*Attesting Officer*

JAMES E. ROGAN
*Director of the United States Patent and Trademark Office*